(12) United States Patent
Holland et al.

(10) Patent No.: US 6,764,451 B2
(45) Date of Patent: Jul. 20, 2004

(54) INFANT CARDIAC AND APNEA HOME MONITORING SYSTEM

(76) Inventors: Teresa C. Holland, 1881 Country-Lane Dr., Greenfield, IN (US) 46140; Mick C. Suskovich, 12131 Madrone Dr., Indianapolis, IN (US) 46236

( * ) Notice: Subject to any disclaimer, the term of this patent is extended or adjusted under 35 U.S.C. 154(b) by 36 days.

(21) Appl. No.: 09/951,119

(22) Filed: Sep. 14, 2001

(65) Prior Publication Data

US 2003/0055350 A1 Mar. 20, 2003

(51) Int. Cl.$^7$ ............................................. A61B 5/205
(52) U.S. Cl. ................................. 600/483; 600/513
(58) Field of Search ................................. 600/483, 513

(56) References Cited

U.S. PATENT DOCUMENTS 5,738,102 A * 4/1998 Lemelson .................. 600/483
6,047,203 A * 4/2000 Sackner et al. ............. 600/483

* cited by examiner

Primary Examiner—Scott M. Getzow
(74) Attorney, Agent, or Firm—Teresa C. Holland; Mick C. Suskovich; Robt. A. Spray

(57) ABSTRACT

An infant cardiac and apnea home monitoring system, which provides audible, visual, and other auxiliary sensory alarms and also includes the ability to transmit an encrypted signal to an Emergency Message Retrieval Unit (EMRU), which in itself contains audible, visual, and touch sensory alarms.

The ability of the Personal Home Baby Monitor (PHBM) to identify when an infant's heart or respiratory rate is not within the pre-set parameters will result in the activation of an alarm state Once the PHBM has entered an alarm state, the base unit will trigger all available alerts, including the simultaneous transmission of a low frequency enable and a high frequency modulated signal, from the base unit to the EMRU. The EMRU upon successfully decoding and validation of the signal will trigger its sensory alarms.

7 Claims, 19 Drawing Sheets

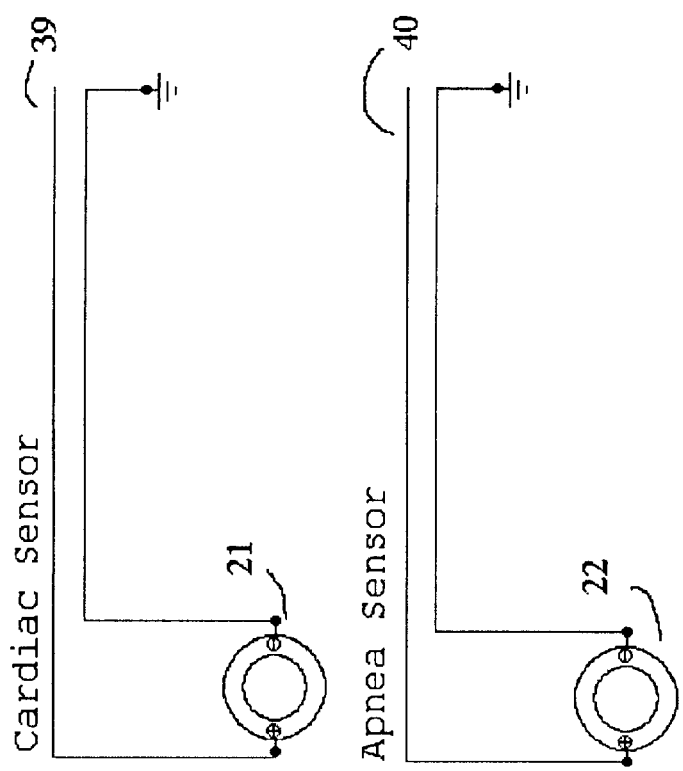

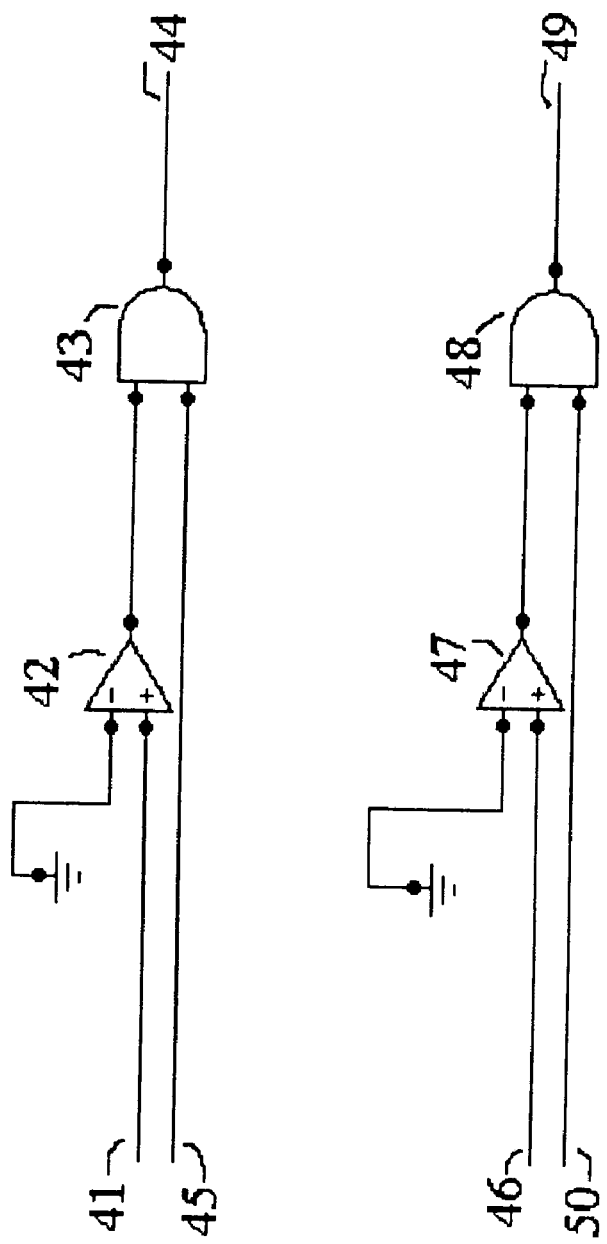

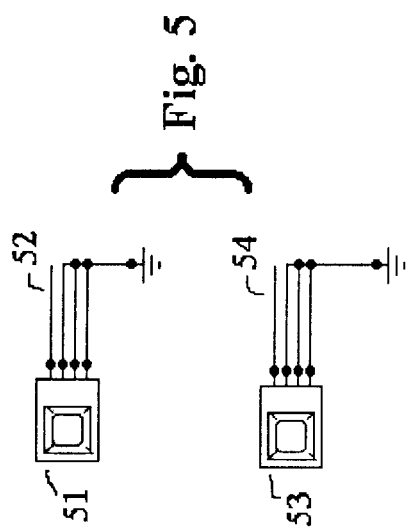
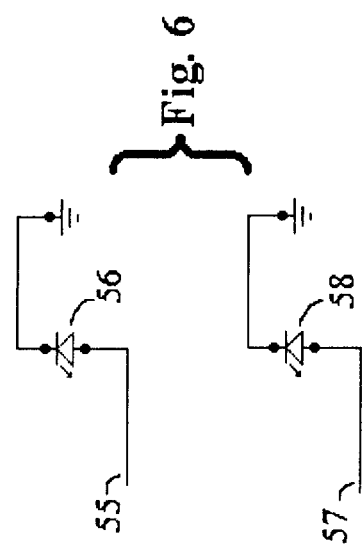

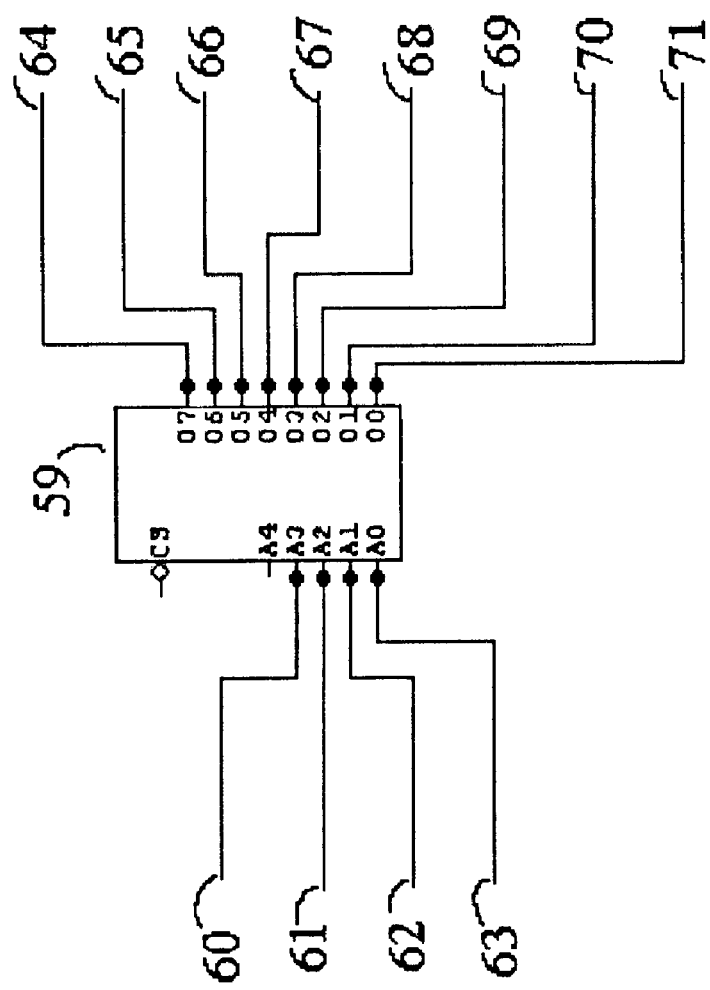

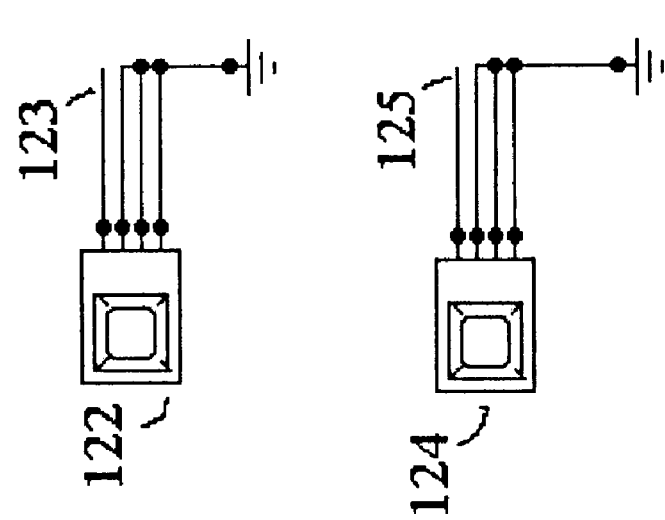

INFANT CARDIAC AND APNEA HOME MONITORING SYSTEM

BACKGROUND

The conceptual idea for the design was initially brought about by the acknowledgement that: parents affected by physical ailments were more challenged to care for newborn children, due to the lack of sufficient monitoring systems. Existing monitoring technologies fail to satisfy the needs of wanting parents.

The focus of the design became based on providing a solution for the dilemma at hand. The overall purpose of the invention is to assure parents who are sensory challenged to be notified of a life-threatening event that requires an emergency response.

SUMMARY

A robust and dynamic system for monitoring young children that allows parents to be notified of a life threatening event that requires an emergency response. The invention encapsulates special considerations for parents who have sensory disabilities. The invention is comprised of three sub systems: A sensory system that utilizes open end electrodes that are physically attached to a young child; A portable base that is connected to the sensory system and monitors the electrical impulses transmitted by the electrodes, manages alarm states, encapsulates and triggers alarms, and also transmits simultaneous high and low frequency signals during alarm states; and an EMRU that receives signals, decodes signals, and triggers alarm states.

Field and Usefulness of the Invention, Briefly

The present invention relates to the home monitoring of infants who are at risk for life-threatening events triggered by alterations of the cardiac or pulmonary systems of the body.

More particularly, the concepts add to the state of home monitoring of cardiac and/or pulmonary art, a valuable system utilizing communication between system parts, and enacting a personal EMRU, which is unique to this system. This invention further establishes a new communication home monitoring cardiac and pulmonary system schema.

The usefulness of this invention provides for increased safety in monitoring of infants, greater mobility, and increased quality of life for those utilizing home cardiac-pulmonary monitoring systems. This system furthermore encapsulates special considerations particularly for those parents experiencing sensory limitations, therefore enabling them to respond to emergency needs as well as those parents who do not experience sensory limitations.

Problems and other Factors Inherent in Infant Cardiac Pulmonary Home Monitoring Systems A long-standing known problem of current patient cardiac pulmonary monitoring systems in inpatient acute care facilities is that current systems utilizing pagers and telemetry systems can and do frequently receive interference from other transmitting objects, such as cell phones or other patient monitors. Thus, precluding current art utilizes permanently installed antennas as part of the systems, rendering the systems non-portable. Accordingly, the present invention deals with problems of inaccurate, interrupted signaling and portability of the monitoring system in relation to patient proximity. Current art of home monitoring systems, to these inventors' knowledge, do not utilize a personal EMRU to verify notification of alert life-threatening events. Current art is burdened by the requirement of constant visualization of a flashing strobe or bed-shaker for those parents who are hearing impaired. The present invention encapsulates special considerations for physically impaired parents, as well as those that are not physically challenged.

Prior Art as Particular Instances of Failure to Provide This Novel System

In view of the vital life saving and high economic advantages achieved generally by the present invention, it may be difficult to realize that the prior art has not conceived of the combination purpose and achievement of the present invention. Even though cardiac and pulmonary infant monitoring systems are widespread, there continues to be a need in the development of more effective systems. Improvements are needed to provide increased safety and an increased quality of life for those utilizing such systems.

The consideration of the nature of the present invention concepts may be helped by a summarized consideration of the prior art as known to the inventors, however, as infant cardiac and apnea monitoring systems are widespread. Various types of infant cardiac and apnea monitoring systems are here conceded, but the nature of the prior art existing for such systems does not provide the overall combinations of the present invention.

Summary of the Prior Art's Lack of Suggestions of the Concepts of the Invention's Combination In spite of all such factors of the prior art knowledge and use, the problem here solved awaited these inventors' consideration, ideas, and creativity. More particularly, as to the novelty here of the invention as considered as a whole, a consideration of the prior art uses and needs helps show its contrast to the concepts, and emphasizes the advantages, novelty, and the inventive significance of the present concepts as are here shown, particularly as to emergency response ability and enhanced quality of life.

Moreover, prior art systems, such as cardiac and pulmonary monitoring systems for home use, as known to these inventors, which could possibly be adapted for this duty, fail to show or suggest the details of the present concepts as a combination; and a realistic consideration of the prior art's differences from the present concepts of the overall combination may more aptly be described as a parallel ideology with a common goal as existing inventions, but existing inventions do not suggest the novel concepts of this invention.

The existence of such prior art knowledge and related ideas which embody such various features is not only conceded, it is emphasized; for as to the novelty here of the combination, of the invention as considered as a whole, a contrast to the prior art helps also to remind of needed improvement, and the advantages and the inventive significance of the present concepts. Thus, as shown herein as a contrast to all the prior art, the inventive significance of the present concepts as a combination is emphasized, and the nature of the concepts and their results can perhaps easier be seen as an invention.

Although varieties of prior art are conceded, and ample motivation is shown, and full capability in the prior art is conceded, no prior art shows or suggests details of the overall combination of the present invention, as is the proper and accepted way of considering the inventiveness nature of the concepts.

That is, although the prior art may show an approach that is parallel to the overall invention, it is determinatively significant that none of the prior art show the novel and advantageous concepts in combination, which provide the merits of this invention.

And the prior art's lack of an invention achieving the inclusion of parents with sensory challenges in response to their child's unexpected life-threatening event, as well as parents who are not physically challenged, merits the improvements and solutions offered by the system of this invention.

BRIEF DESCRIPTION OF THE DRAWINGS

The above description of the novel and advantageous invention is of somewhat introductory and generalized form. More particular details, concepts and features are set forth in the following and more detailed description of the preferred embodiment, taken in conjunction with the accompanying drawings which are of somewhat schematic and diagrammatic nature for showing the inventive concepts; and more particularly;

FIG. 3 shows Cardiac/Apnea Sensory circuitry for each of cardiac and apnea circuitry;

FIG. 4 shows Sensory Interface circuitry for amplifying the signals from each the cardiac and apnea circuits;

FIG. 5 shows the power and reset buttons of the circuitry of both the cardiac and apnea circuits;

FIG. 6 shows indicator Light Emitting Diodes (LED(s)) of each of the cardiac and apnea circuits;

FIG. 7 shows a programmable logic chip that receives input from the power button, reset button, cardiac and apnea circuitry; and also signals to indicator lights, signal transmitters, audio speaker, auxiliary ports, and enable circuitry;

FIG. 20 shows the power and reset buttons of the circuitry

DESCRIPTION OF THE PREFERRED EMBODIMENT

Figure 1:
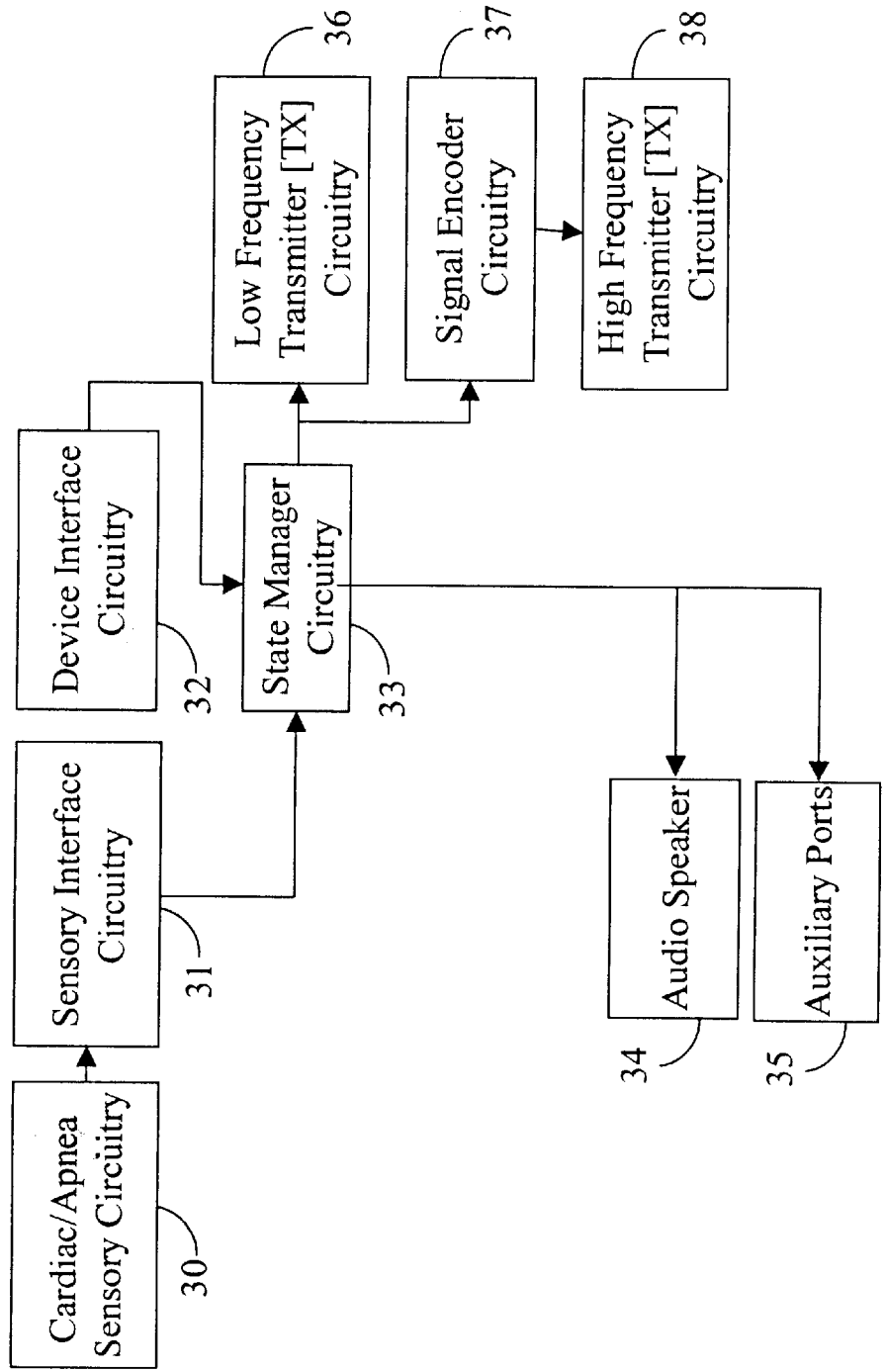
FIG. 1 is a so-called block diagram of the overall circuitry and components of the monitoring base apparatus.

As shown in the drawings, the details of the circuitry and components are shown for a preferred embodiment, providing and achieving the advantageous monitoring apparatus useful particular for the safety monitoring of cardiac and apnea dangers.

Figure 2:
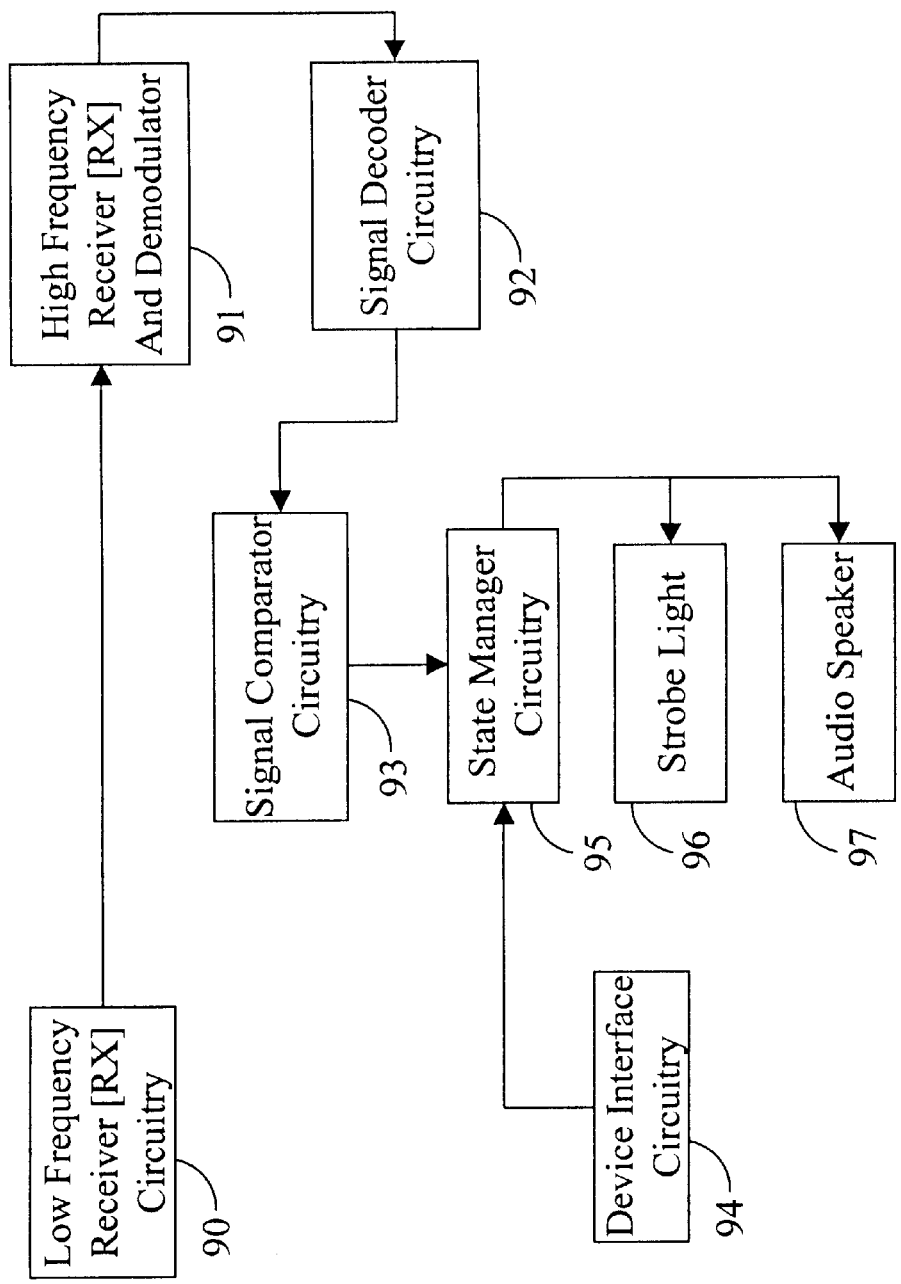
FIG. 2 is a block diagram of the circuitry and components of the EMRU apparatus.

More particularly the overall apparatus is shown in FIGS. 1 and 2, they being functional representations utilizing circuitry and components shown illustratively in the FIGS. 3–20.

The system 30 as shown in FIG. 1 is the cardiac/apnea sensory circuitry, and as shown is comprised in part by the elements detailed in FIG. 3 and constitutes two electrodes 21 and 22, connecting wires, and cable utilized for measuring heart and respiratory rates. The make up and utilization of the electrodes, connecting wires, and cable are conceded as prior art. Electronic impulses generated by the human body are propagated through the wires 39 and 40 for cardiac and apnea respectively.

The system 31 as shown in FIG. 1 is the sensory interface circuitry, shown as being comprised by the elements detailed in FIG. 4. The signals propagated on wires 39 and 40 respectively are connected to wires 41 and 46 respectively which lead to operational amplifiers 42 and 47 respectively that will amplify signal polarities and strengths as may be determined by physical design requirements, such as deviations in component operation, impedance matching, and electrode sensitivity, etc. After the cardiac and apnea signals have been amplified, they are further propagated to AND gates 43 and 48 respectively. When the signals propagated via wires 45 and 50 (connected to wires 70 and 71 respectively, described below) are in an active state the amplified signals are propagated via 44 and 49 respectively.

The system 32 as shown in FIG. 1 constitutes the device interface circuitry, being comprised in part by the elements detailed in FIG. 5 and FIG. 6. FIG. 5 consists of two electronic switches 51 and 53 being 'POWER' and 'SYSTEM RESET' respectively. When either switch is depressed wires 52 and 54 connected to wires 62 and 63 (wires 62 and 63 are described below) are brought down to ground state. FIG. 6 consists of two light emitting diodes 56 and 58 as cardiac and apnea signal indicator lights respectively. These lights indicate emergency situations in regards to cardiac and apnea aberrant episodes respectively. Wires 55 and 57 are connected to wires 64 and 65 (wires 64 and 65 are describe below). Wires 64 and 65 propagate the cardiac alert and apnea alert signals respectively.

The system 33 as shown in FIG. 1 constitutes the state manager circuitry, being comprised by the elements detailed in FIG. 7. FIG. 7 shows a programmable logic chip 59. The system 33 receives input signals: cardiac signal via wire 60 connected to wire 44; apnea signal via wire 61 connected to wire 49; system reset signal via wire 62 connected to wire 54; and power 'on' and 'off' signal via wire 63 connected to wire 52. The system 33 sends signals: cardiac alert via wire 64; apnea alert via wire 65; alarm state via wire 66; low frequency enable via wire 67; auxiliary enable via wire 68; audio enable via wire 69; apnea sensor enable via wire 70; and cardiac sensor enable via wire 71. Connections for wires 64 through 71 are detailed below.

Figure 8:
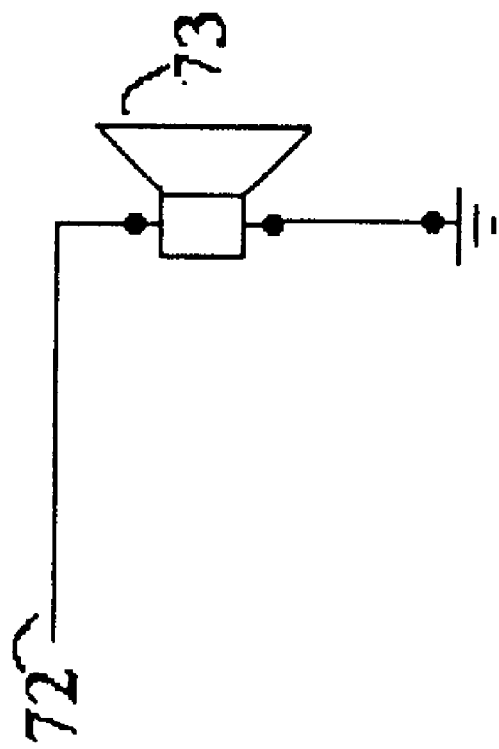
FIG. 8 shows an audio speaker.

The system 34 as shown in FIG. 1 is comprised by the elements detailed in FIG. 8, which constitutes an audio speaker 73. Wire 72 is connected to wire 69 (Wire 69 propagates the audio enable signal). The audio enable signal is active when the system has determined that either a cardiac or apnea aberrant episode has occurred.

Figure 9:
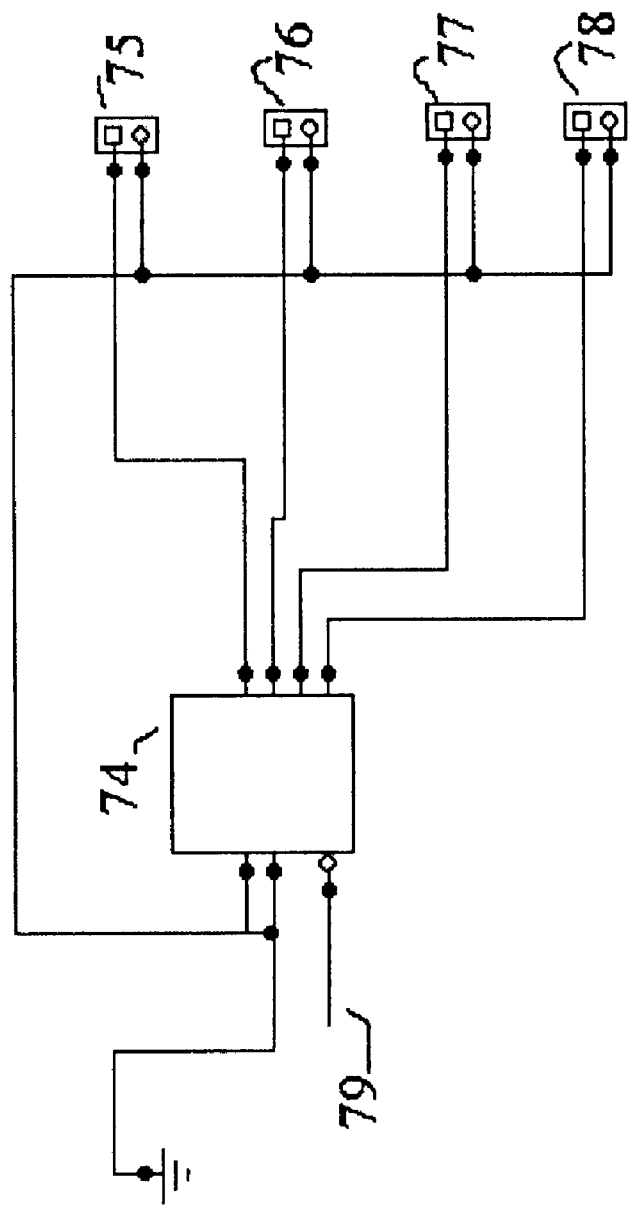
FIG. 9 shows a multiplexer chip for switching auxiliary ports for powering external peripherals.

The system 35 as shown in FIG. 1 constitutes the auxiliary port circuitry as being comprised by the elements detailed in FIG. 9. FIG. 9 shows a multiplexer 74 and auxiliary ports 75–78. The wire 79 is connected to wire 68.

Figure 10:
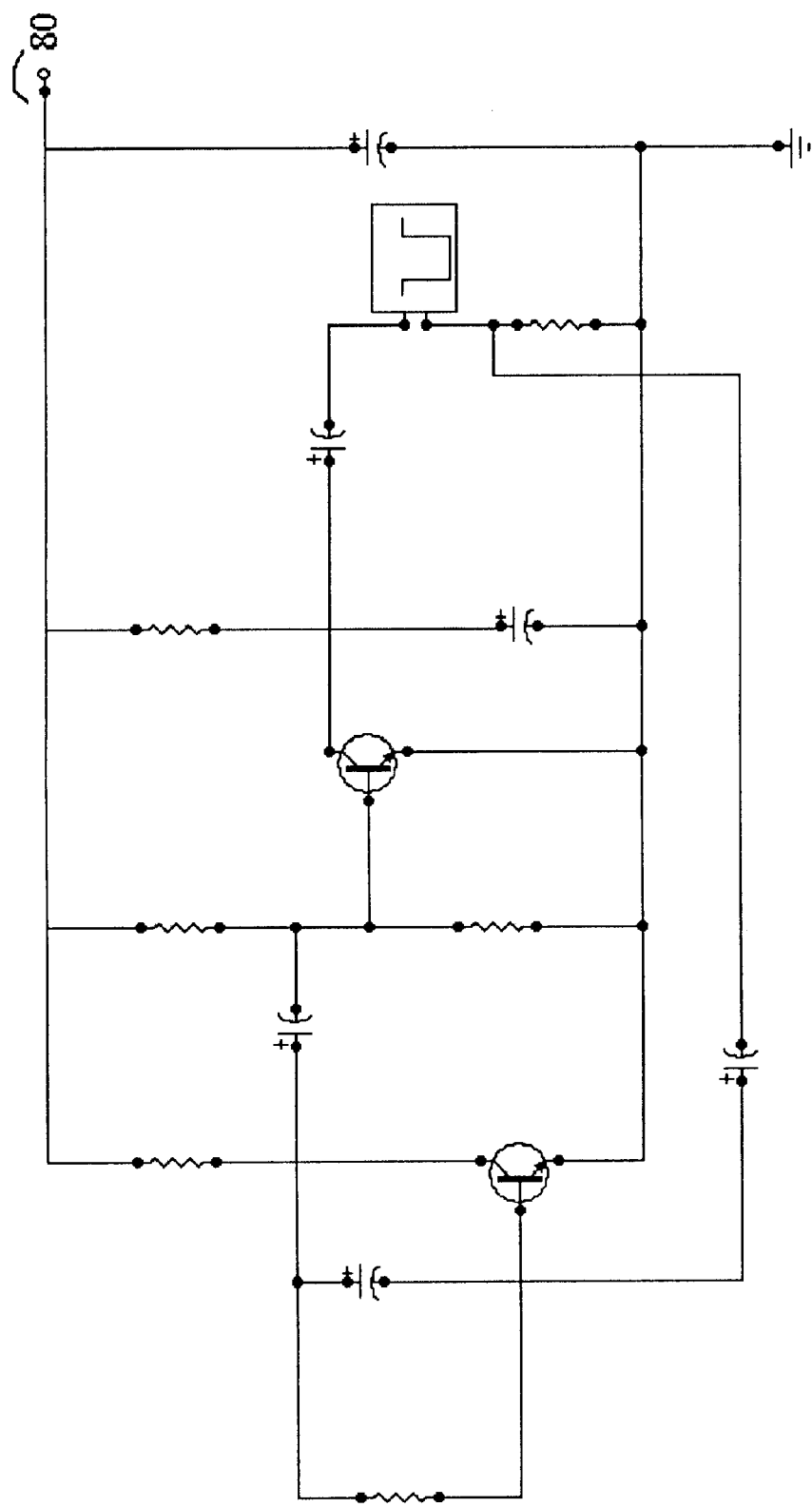
FIG. 10 shows a low frequency transmitter.

The system 36 as shown in FIG. 1 being comprised in part by the elements detailed in FIG. 10 constitute the low frequency transmitter. The wire 80 is connected to wire 67.

Figure 11:
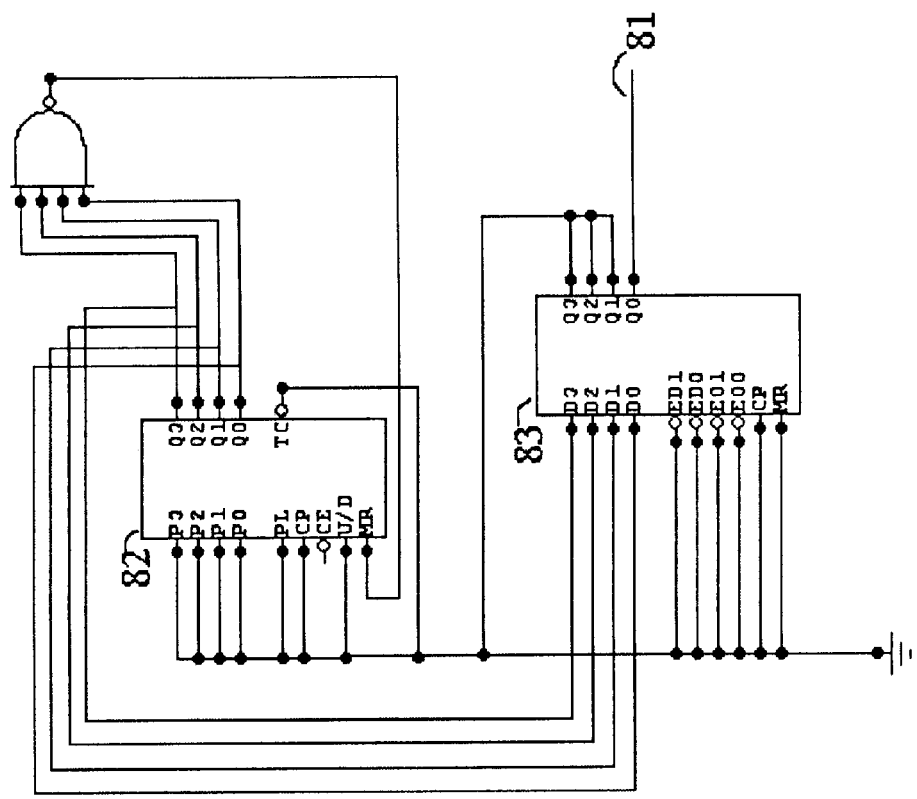
FIG. 11 shows a signal encoder circuitry having a counter chip, a register chip, and a NAND gate.

The system 37 as shown in FIG. 1 being comprised in part by the elements detailed in FIG. 11 constitutes the high frequency encoder. FIG. 11 is comprised of a counter chip 83, a register chip 82, and a NAND gate. The counter chip iterates through a repeating numerical sequence. The output of the counter chip is the input to the register. The register outputs the value of the memory address of its corresponding input value input to wire 81.

Figure 12:
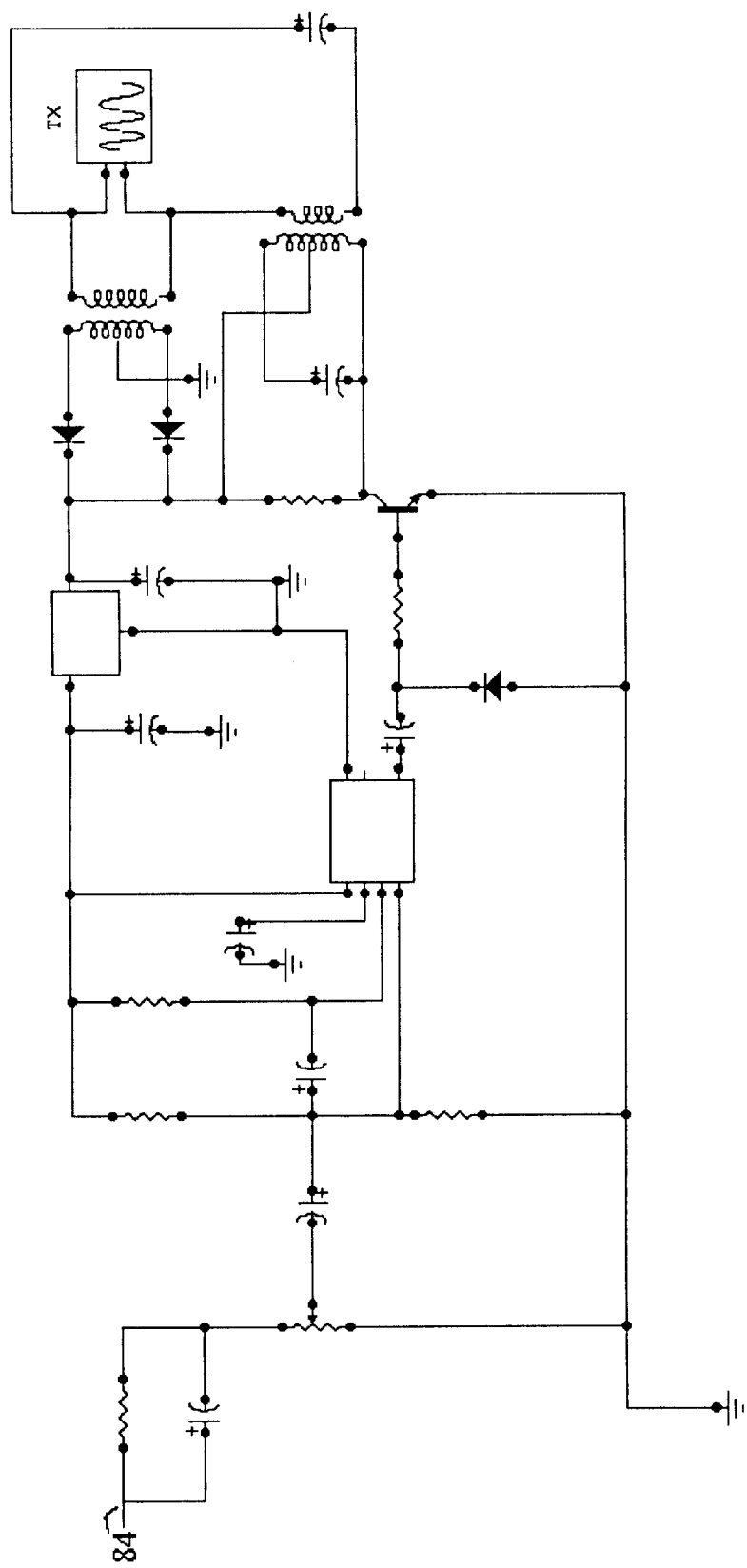
FIG. 12 shows a signal modulator and high frequency transmitter circuitry.

The system 38 as shown in FIG. 1 being comprised in part by the elements detailed in FIG. 12 constitutes the high frequency transmitter. The wire 84 is connected to wire 81. The circuit modulates the signal carried via the wire and further transmits the carrier signal.

Figure 13:
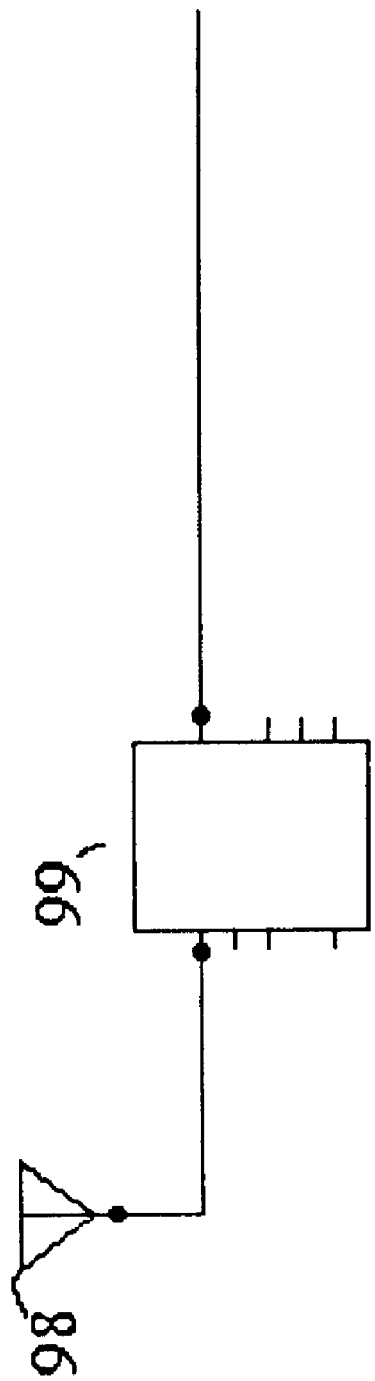
FIG. 13 shows a low frequency signal receiver.

The system 90 as shown in FIG. 2 being comprised in part by the elements detailed in FIG. 13 constitutes the low frequency receiver. The low frequency receiver is comprised of an antenna 98 and a phased lock loop 99.

Figure 14:
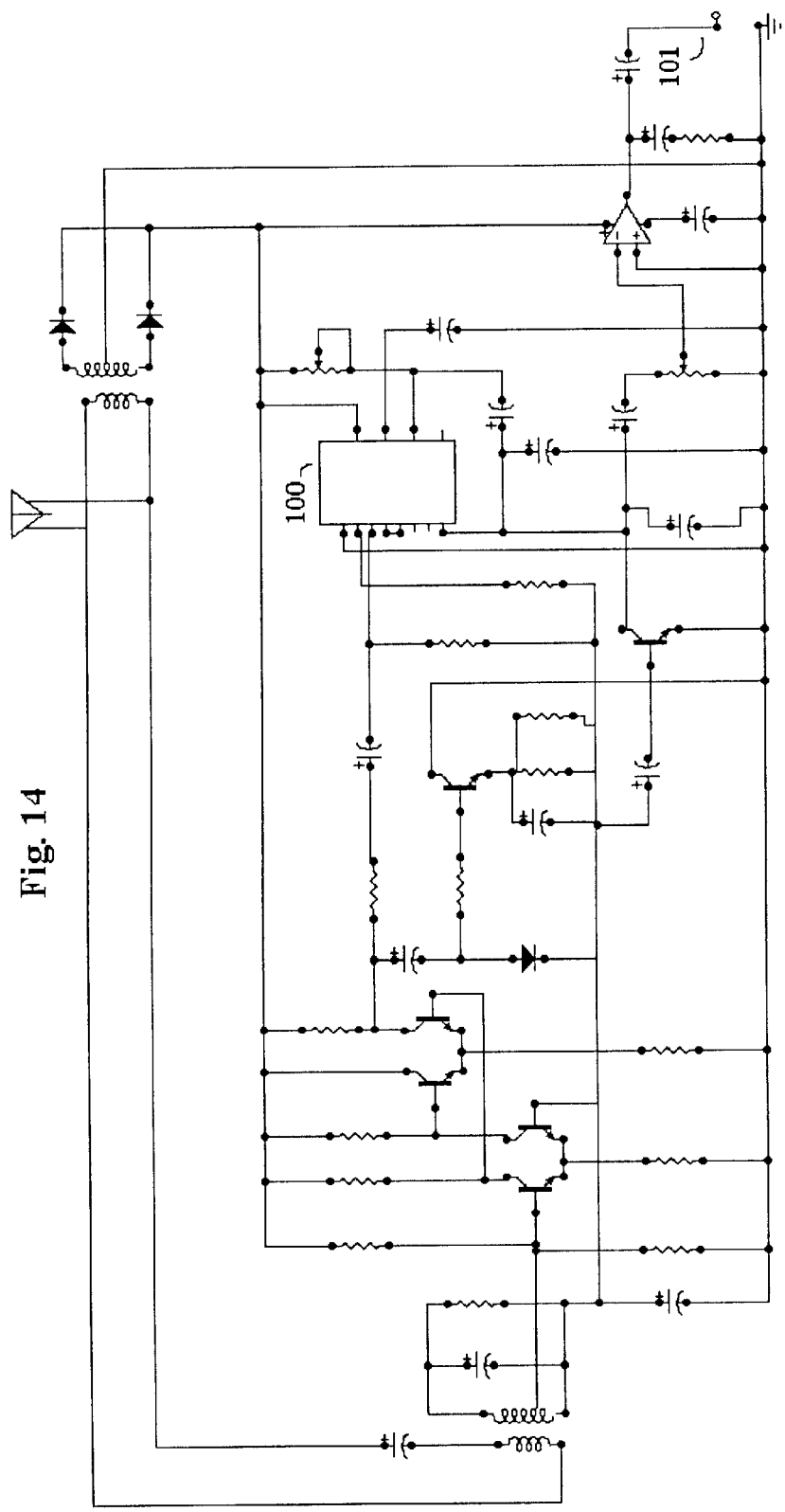
FIG. 14 shows high frequency signal receiving circuitry and signal demodulator.

The system 91 as shown in FIG. 2 being comprised in part by the elements detailed in FIG. 14 constitutes the high frequency receiver. The high frequency receiver detects the carrier signal, demodulates the signal. The demodulated signal is propagated via wire 101.

Figure 15:
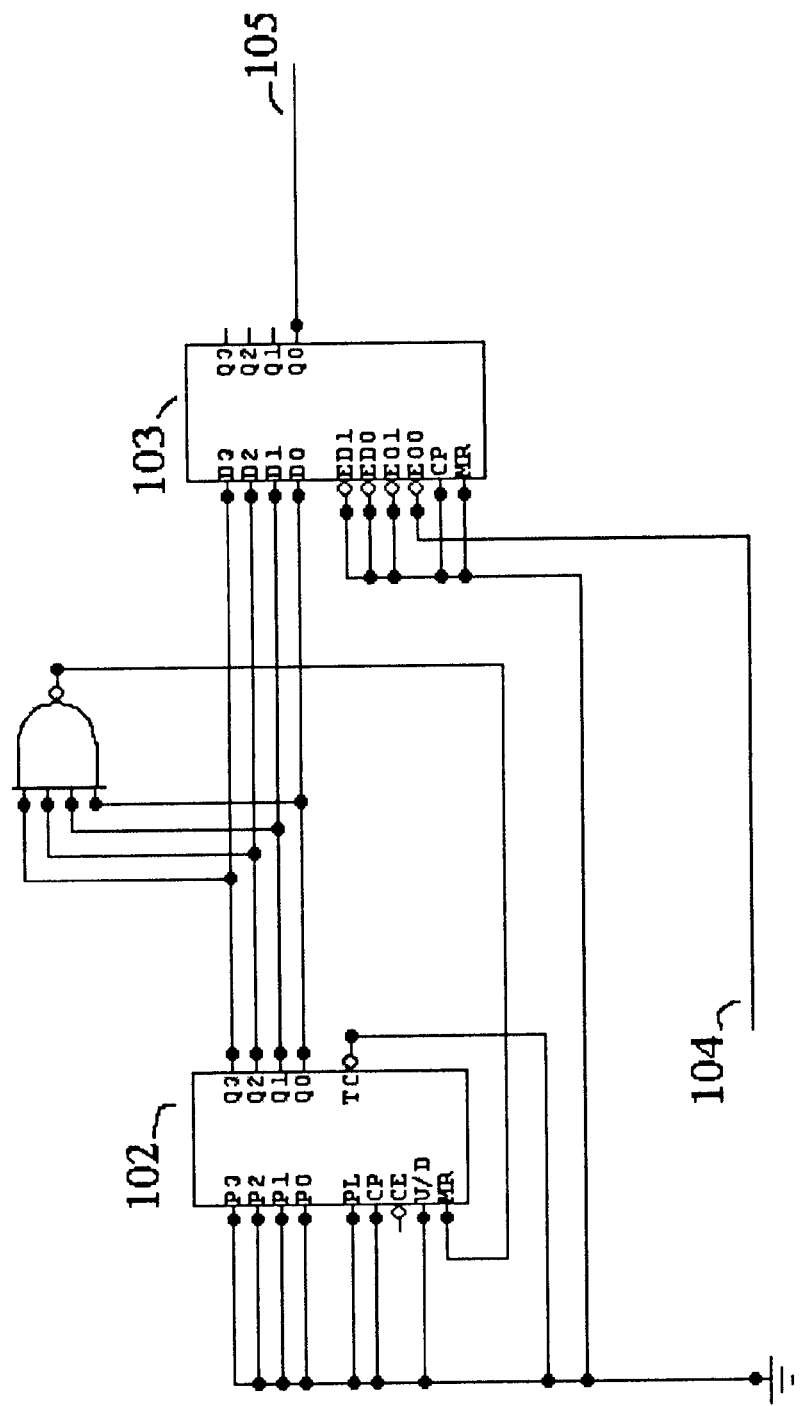
FIG. 15 shows a signal decoding circuitry having a counter chip, a register chip, and a NAND gate.

The system 92 as show in FIG. 2 being comprised in part by the elements detailed in FIG. 15 constitutes the high frequency decoder. The high frequency decoder is comprised of a register chip 103, counter chip 102, and a NAND gate. Wire 104 is connected to wire 101. The signal propagated on wire 104 is the input to the register. For each value the counter chip outputs the register has a corresponding memory location. As the counter chip iterates the values propagated on wire 104 are stored in corresponding memory locations.

Figure 16:
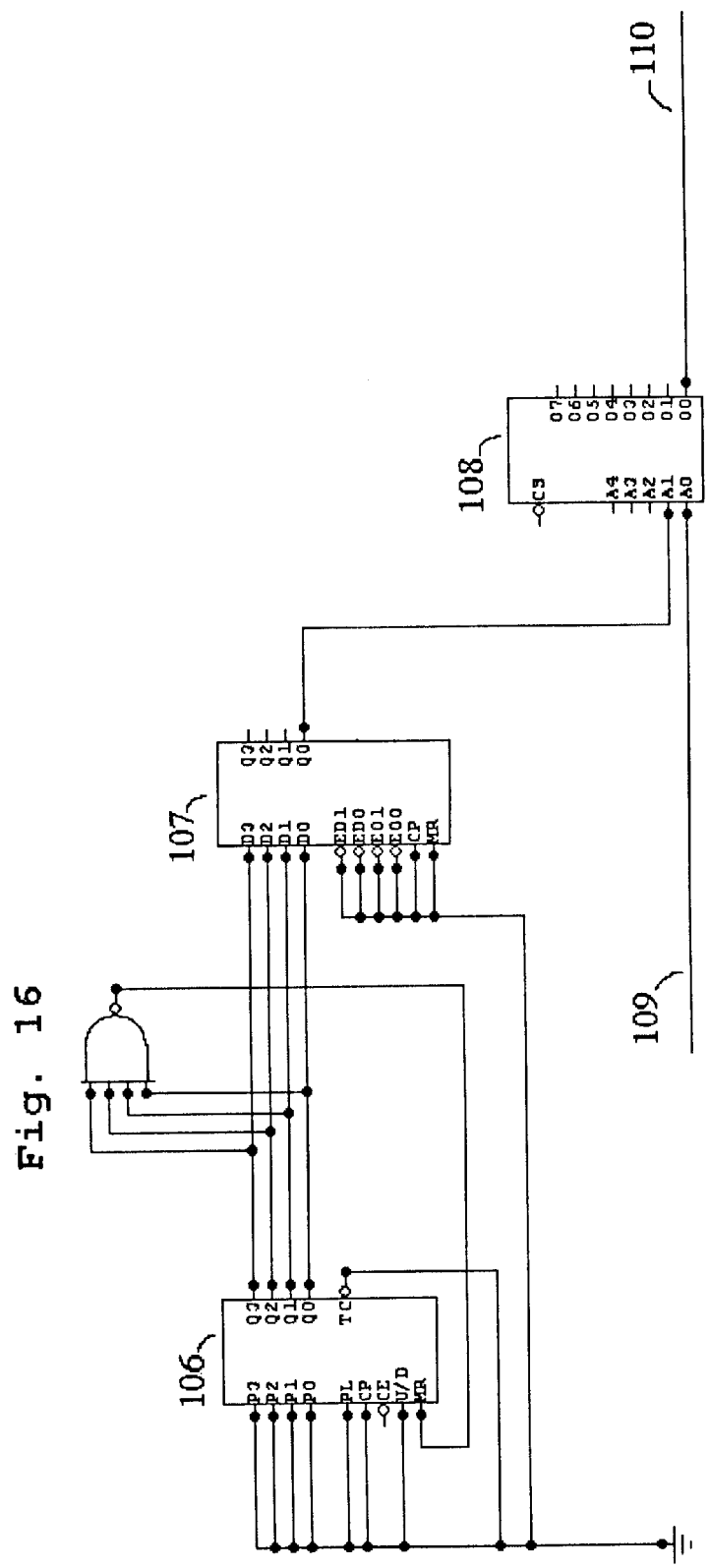
FIG. 16 shows signal comparison circuitry having a counter chip, a register chip, a NAND gate, and a Programmable Logic chip.

The system 93 as shown in FIG. 2 being comprised in part by the elements detailed in FIG. 16 constitutes the registry comparator. The registry comparator is comprised of a counter chip 106, a register chip 107, a comparator chip 108 and a NAND gate. Wire 109 is connected to wire 105. The comparator evaluates the signals that are propagated via wire 109 and the output of the register chip. The resultant value is propagated via wire 110.

Figure 17:
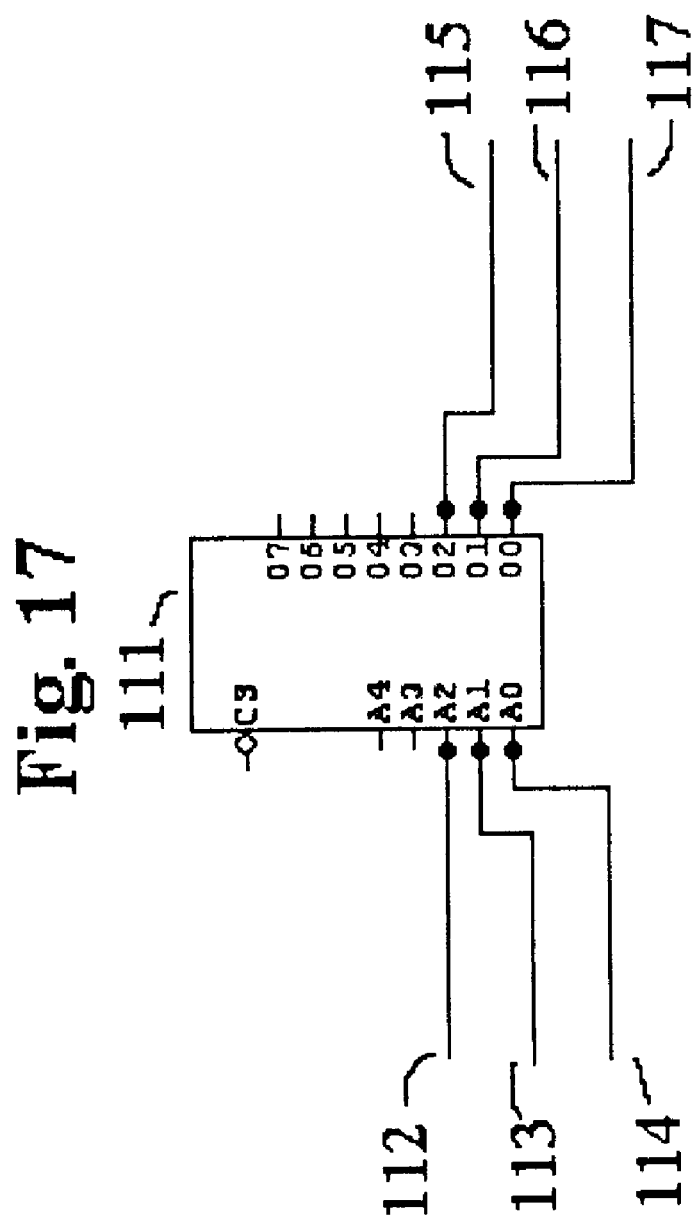
FIG. 17 shows a programmable logic chip that receives input from the power button, reset button, and signal receiver circuitry; and also signals to indicator lights, audio speaker.

The system 94 as shown in FIG. 2 being comprised in part by the elements detailed in FIG. 17 constitutes the state management of the Emergency Message Retrieval Unit (EMRU). Being comprised of a programmable logic chip 111. The EMRU receives input signal comparator output 110 connected to wire 112, power on and off propagated on wire 123 connected to wire 113, reset propagated on wire 125 connected to wire 114. The system sends output data: audio enable via wire 115, light enable via wire 116, and alarm state via wire 117.

Figure 18:
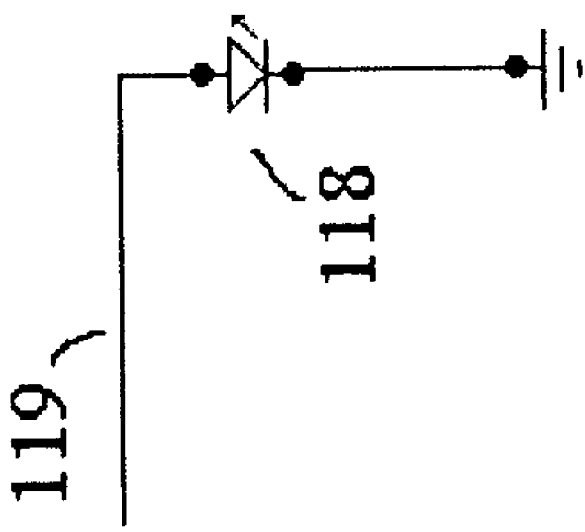
FIG. 18 shows a light emitting diode (LED)

The system 96 as shown in FIG. 2 being comprised in part by the elements detailed in FIG. 18 constitutes the indicator light. The indicator light is comprised of a light emitting diode (LED) 118.

Figure 19:
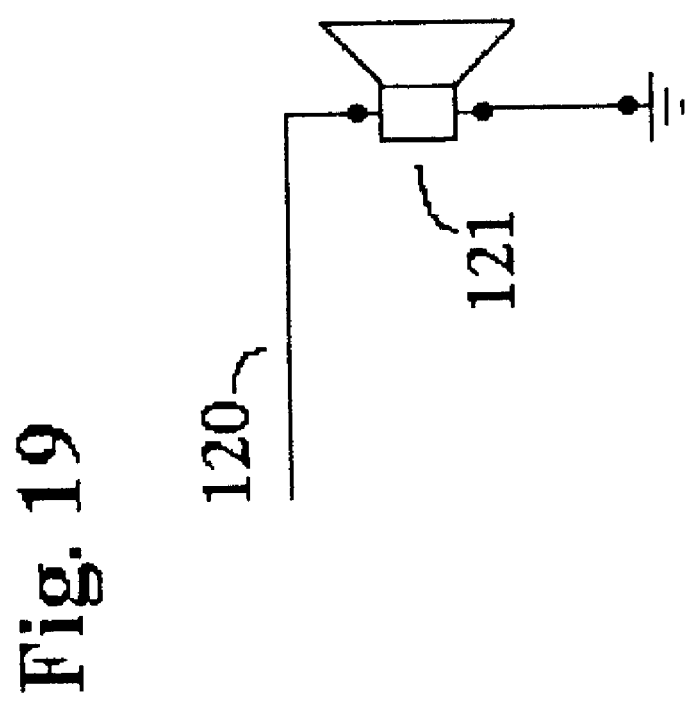
FIG. 19 shows an audio speaker.

The system 97 as shown in FIG. 2 being comprised in part by the elements detailed in FIG. 19 constitutes the audio speaker 121. Wire 120 is connected to wire 115.

The system 94 as show in FIG. 2 being comprised in part by the elements detailed in FIG. 20 constitutes the EMRU device interface. FIG. 20 consists of two electronic switches 122 and 124 begin 'Power' and 'Reset' respectively. When either switch is depressed a signal is propagated via wires 123 and 125 respectively.

Modifications and variations may effected without departing from the scope of the novel concepts of the invention; accordingly, the invention is not limited to the specific form or arrangement of parts herein described or shown.

What is claimed is:

1. An alarm state manager system of the human body's pulmonary and cardiac systems having cardiac and apnea detection means for carrying electrical impulses from a pair of monitoring sensors operatively connected to the human body, and having a base receiving means operatively connected to the monitoring sensors; and having base analyzing means which analyzes variations of electrical impulse signals from the respective monitoring sensors and having an alarm state manager means for switching an alarm action means in response to the signals received by the base receiving means and analyzed by the base analyzing means;

Base audio warning means for sounding an audio alarm;

Base visual warning means for illuminating visual alarm;

Alarm action means being comprised of signal warning transmit means, base audio warning means, and base visual warning means;

EMRU enable receiving means for receiving an enable signal transmitted by signal warning transmit means;

EMRU modulated receiving means for receiving a modulated carrier signal containing a binary code;

EMRU signal register means for holding short-term data in memory;

EMRU signal demodulator means which demodulates the carrier signal and stores short-term memory data in signal register means;

EMRU signal comparator means performing Boolean comparisons of demodulated data against binary code within EMRU;

EMRU audio warning means for sounding an audio alarm;

EMRU visual warning means for illuminating a visual alarm;

EMRU motion warning means for creating vibratory movement alarm;

EMRU alarm action means comprised of EMRU audio, visual, and motion warning means;

EMRU alarm state manager means for switching EMRU alarm action means in response to said EMRU signal comparator means when a matching binary code is detected.

2. The invention as set forth in claim 1 in a combination in which said cardiac and apnea detection means actuates the said base receiving means by receiving electrical impulses via conducting wires connected to the body.

3. The invention as set forth in claim 1 in a combination in which said base receiving means receives electrical impulses from the said cardiac and apnea detection means and actuates signals to said base analyzing means which detects if the received signals are within system parameters of the alarm state manager system.

4. The invention as set forth in claim 1 in a combination in which said base analyzing means has detected actuated signals exceeding preset parameters, this impulse actuated the enabling function of the EMRU.

5. The invention as set forth in claim 4 in a combination in which said alarm action means, which controls actuation of the EMRU and signal warning transmit means.

6. The invention as set forth in claim 5 in a combination in which, when said alarm state manager means actuates the modulation of a unique binary code into a carrier signal and transmits signal to the EMRU and actuates the invention as set forth in claim 1.

7. The invention as set forth in claim 6 in which said Emergency Message Retrieval Unit (EMRU) is comprised of said enable receiving means receiving enable signal from the said signal warning transmit means; and said EMRU modulated receiving means to initiate receiving of carrier signal from said signal warning transmit means and EMRU signal register means for storing short-term memory data from EMRU signal demodulator means; also including said EMRU signal comparator means for comparing data from EMRU signal demodulator means and binary code unique to the alarm state manager system; said EMRU alarm state manager system means initiates switching when said comparator detects match, further actuating binary code match to said EMRU alarm action means, which will actuate and/or EMRU audio, visual, or vibratory warning means.

\* \* \* \* \*